(12) United States Patent
Adkins et al.

(10) Patent No.: US 7,666,971 B2
(45) Date of Patent: Feb. 23, 2010

(54) AMIDE/UREA-MODIFIED LIQUID DIPHENYLMETHANE DIISOCYANATES

(75) Inventors: Rick L. Adkins, Hurricane, WV (US); William E. Slack, Moundsville, WV (US)

(73) Assignee: Bayer MaterialScience LLC, Pittsburgh, PA (US)

(*) Notice: Subject to any disclaimer, the term of this patent is extended or adjusted under 35 U.S.C. 154(b) by 86 days.

(21) Appl. No.: 11/599,101

(22) Filed: Nov. 14, 2006

(65) Prior Publication Data
US 2008/0139777 A1 Jun. 12, 2008

(51) Int. Cl.
*C08G 18/70* (2006.01)
(52) U.S. Cl. .......................... 528/67; 564/248
(58) Field of Classification Search .............. 528/67; 564/248
See application file for complete search history.

(56) References Cited

U.S. PATENT DOCUMENTS

| | | | | |
|---|---|---|---|---|
| 4,318,861 A | * | 3/1982 | Babiec et al. | 560/332 |
| 4,331,810 A | | 5/1982 | Christman et al. | |
| 6,242,556 B1 | * | 6/2001 | Markusch et al. | 528/67 |
| 6,475,366 B1 | | 11/2002 | Nishiguchi et al. | 204/505 |
| 6,730,405 B2 | | 5/2004 | Bernard et al. | 428/423.1 |

* cited by examiner

*Primary Examiner*—Karl J Puttlitz
*Assistant Examiner*—Sudhakar Katakam
(74) *Attorney, Agent, or Firm*—N. Denise Brown; Noland J. Cheung

(57) ABSTRACT

This invention relates to novel liquid, storage-stable, amide-modified diphenylmethane diisocyanates and to a process for the production of these liquid, storage-stable diphenylmethane diisocyanates.

22 Claims, No Drawings

AMIDE/UREA-MODIFIED LIQUID DIPHENYLMETHANE DIISOCYANATES

BACKGROUND OF THE INVENTION

This invention relates to novel amide- and urea-modified liquid diphenylmethane diisocyanate compositions and to a process for the preparation of these novel amide-modified liquid diisocyanate compositions.

Polyisocyanate compositions exhibiting low viscosities and high functionalities and a process for their preparation are disclosed in U.S. Pat. No. 6,730,405. These polyisocyanate compositions may be reacted with a compound comprising a mobile hydrogen, which are also known as masking agents. Masking agents are described as having at least one functional group carrying a mobile (or reactive) hydrogen, and the functional group should have a pKa of at least 4 to less than or equal to 14.

U.S. Pat. No. 6,475,366 discloses cationically electrodepositable coating compositions. These coating compositions comprise as a cross-linking agent, a blocked polyisocyanate having at least 0.1 blocked isocyanate group represented by the formula:

$$NH-CO-N\begin{array}{c}R_2\\COR_1\end{array}$$

in which $R_1$ represents a hydrogen atom, or a methyl, ethyl or propyl group; and $R_2$ represents a methyl or ethyl group. One of the coating compositions described comprises a cationic resin having an active hydrogen group capable of reacting an isocyanate group as a base resin and the blocked polyisocyanate described above as an external cross-linking agent. Another coating composition as described in U.S. Pat. No. 6,475,366 is a thermosetting cationically electrodepositable coating composition comprise as the base resin, a cationic resin of a self cross-linking type having both the blocked isocyanate group as set forth above and an active hydrogen group in a molecule.

It has surprisingly been found that diisocyanates which are modified with amides as described herein are low viscosity liquid products which are storage stable at room temperature. It has also been found that these modified diisocyanates exhibit lower freezing points than the corresponding unmodified diisocyanates. Advantages of these modified diisocyanates include the ability of store and use them in processes without the need to maintain a >25° C. storage temperature.

SUMMARY OF THE INVENTION

This invention relates to liquid, storage-stable diisocyanates having an NCO group content of 11 to 32% by weight, and to a process for the preparation of these liquid, storage-stable diisocyanates.

These liquid, storage-stable diisocyanates comprise the reaction product of: (A) diphenylmethane diisocyanate, with (B) at least one compound selected from the group consisting of an amide, a bisamide and a cyclic urea, each of which correspond to a specified formula.

The diphenylmethane diisocyanate (A) comprises:
(1) from 0 to 6% by weight of the 2,2'-isomer,
(2) from 0 to 60% by weight of the 2,4'-isomer, and
(3) from 34 to 100% by weight of 4,4'-isomer, wherein the sum of the %'s by weight of (1), (2) and (3) totals 100% by weight of (A) the diphenylmethane diisocyanate.

Component (B) comprises at least one compound selected from the group consisting of:
(1) amides which correspond to the structure:

$$RHN-\overset{O}{\underset{\|}{C}}-R_1 \quad (I)$$

wherein:
R: represents a hydrogen atom, an alkyl radical containing from 1 to 5 carbon atoms, a cycloalkyl radical containing from 5 to 6 carbon atoms, or an aryl radical containing 6 carbon atoms;
and
$R_1$: represents a hydrogen atom, an alkyl radical containing from 1 to 6 carbon atoms, a cycloalkyl radical containing from 5 to 6 carbon atoms, an aryl radical containing 6 carbon atoms, or an alkoxy radical;
with the proviso that R and $R_1$ do not simultaneously represent hydrogen;

(2) bisamide which correspond to the structure:

$$R_2-\overset{O}{\underset{\|}{C}}-NH-R_3-NH-\overset{O}{\underset{\|}{C}}-R_2 \quad (II)$$

wherein:
each $R_2$: independently represents a hydrogen atom, an alkyl radical containing from 1 to 6 carbon atoms, a cycloalkyl radical containing 5 or 6 carbon atoms, an alkoxy radical, or an aryl radical containing 6 carbon atoms;
and
$R_3$: represents an alkyl radical containing from 1 to 12 carbon atoms or a cycloalkyl radical containing 6 carbon atoms;
and
(3) cyclic ureas which correspond to the structure:

$$\underset{HN\diagdown\diagup NH}{\overset{O}{\underset{\|}{C}}}_n \quad (III)$$

wherein:
n: represents from 2 to 5 methylene groups.

The process for producing these liquid, storage-stable diisocyanates comprises reacting (A) diphenylmethane diisocyanate, with (B) at least one compound selected from the group consisting of an amide, a bisamide and a cyclic urea, each of which correspond to the formulas specified above, in the presence of at least one catalyst.

In an alternate embodiment of the present invention, the liquid, storage-stable diisocyanates of the present invention may also comprise the reaction product of (A) a diphenylmethane diisocyanate, with a mixture of (B) at least one compound selected from the group consisting of an amide, a bisamide and a cyclic urea, each of which correspond to the formulas specified above, and (C) at least one component selected from the group consisting of aliphatic alcohols having from 1 to 32 carbon atoms and aromatic alcohols having from 6 to 10 carbon atoms.

DETAILED DESCRIPTION OF THE INVENTION

As used in the present invention, the term liquid means that the amide-modified diisocyanate or polyisocyanate product does not precipitate solids when stored at 25° C. for 3 months.

As used herein, the term "storage-stable" means that the amide-modified diisocyanate or polyisocyanate product has up to a 1% absolute change in the % NCO group content and up to a 10% change in the viscosity when stored at 25° C. for 3 months.

The liquid, storage stable, amide-modified diisocyanates of the present invention are typically characterized by an NCO group content of at least about 11% NCO, and preferably of at least about 14% NCO. These liquid diisocyanates are also typically characterized by an NCO group content or less than or equal to about 32% NCO, and preferably less than or equal to about 30% NCO. The liquid modified diisocyanates may also have an NCO group content ranging between any combination of these upper and lower values, inclusive. For example, the liquid diisocyanates may have an NCO group content of from about 11% by weight NCO to about 32% by weight NCO and preferably from about 14% by weight NCO to about 30% by weight NCO.

In accordance with the present invention, the following components are, generally speaking, suitable.

Suitable diisocyanates to be used as component (A) herein include comprise diphenylmethane diisocyanate in which the 2,2'-isomer is present in an amount of from 0 to 6% by weight, and preferably 0 to 2% by weight; the 2,4'-isomer is present in an amount of 0 to 60% by weight, and preferably 1 to 30% by weight; and the 4,4'-isomer is present in an amount of from 34 to 100% by weight, and preferably 68 to 99% by weight. When mixtures of the 2,2'-isomer, the 2,4'-isomer and the 4,4'-isomer of diphenylmethane diisocyanate are used, the sum of the %'s by weight of the individual isomers totals 100% by weight of the diphenylmethane diisocyanate.

Suitable compounds to be used as component (B) in accordance with the present invention include at least one compound selected from the group consisting of:
(1) amides which correspond to the structure:

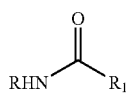

(I)

wherein:
R: represents a hydrogen atom, an alkyl radical containing from 1 to 5 carbon atoms, a cycloalkyl radical containing from 5 to 6 carbon atoms, or an aryl radical containing 6 carbon atoms, and preferably an alkyl radical containing 1 to 3 carbon atoms;
and
$R_1$: represents a hydrogen atom, an alkyl radical containing from 1 to 6 carbon atoms, a cycloalkyl radical containing from 5 to 6 carbon atoms, an aryl radical containing 6 carbon atoms, or an alkoxy radical, and preferably an alkyl radical containing from 1 to 3 carbon atoms;

with the proviso that R and $R_1$ do not simultaneously represent hydrogen;
(2) bisamides which correspond to the structure:

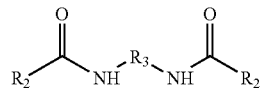

(II)

wherein:
each $R_2$: independently represents a hydrogen atom, an alkyl radical containing from 1 to 6 carbon atoms, a cycloalkyl radical containing 5 or 6 carbon atoms, an alkoxy radical, or an aryl radical containing 6 carbon atoms, and preferably an alkyl radical containing from 1 to 3 carbon atoms;
and
$R_3$: represents an alkyl radical containing from 1 to 12 carbon atoms or a cycloalkyl radical containing 6 carbon atoms, and preferably an alkyl radical containing from 2 to 6 carbon atoms;
and
(3) cyclic ureas which correspond to the structure:

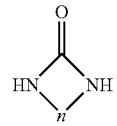

(III)

wherein:
n: represents from 2 to 5 methylene groups.

Some examples of compounds which are suitable to be used as (B)(1) amides herein include N-methylformamide, N-ethylformamide, N-cyclohexylformamide, N-phenylformamide, acetamide, N-methyl-acetamide, N-ethylacetamide, N-methylpropionamide, N-methylcyclo-hexanecarboxamide, N-methylbenzamide, etc. Preferred are N-methylformamide and N-methylacetamide.

Examples of some suitable compounds which can be used as (B)(2) bisamides herein include N,N'-ethylenebisformamide, N,N'-diacetylethylenediamine, N,N'-ethylenebis(cyclohexanecarboxamide), N,N'-ethylenebisbenzamide, N,N'-bis(methoxycarbonyl)-1,2-ethane-diamine, N,N'-1,2-diacetylhexamethylenediamine, etc. Preferred are N,N'-diacetylethylenediamine, and N,N'-1,2-diacetylhexamethylenediamine.

Some examples of compounds which are suitable to be used as (B)(3) cyclic ureas in accordance with the present invention include 2-imidazolidone, propyleneurea, tetramethyleneurea, etc. Preferred is 2-imidazolidone.

In a preferred embodiment of the invention, it is preferred to react from 0.01 equivalent of component (B) per equivalent of component (A) up to 0.5 equivalent of component (B) per equivalent of component (A) in preparing the liquid, storage stable, modified diisocyanates of the invention. It is preferred that from 0.03 to 0.20 equivalent of component (B) per equivalent of component (A) is present.

Suitable components to be used as component (C) herein include compounds selected from the group consisting of aliphatic alcohols having from 1 to 32 carbon atoms and aromatic alcohols having from 6 to 10 carbon atoms. More specifically, such aliphatic alcohols to be used in the present invention include those aliphatic alcohols containing from 1 to 32, and preferably from 4 to 8 carbon atoms. Illustrative but nonlimiting examples of the aliphatic alcohols can be selected from the group consisting of cycloaliphatic alcohols, aliphatic alcohols containing groups that do not react with isocyanates, e.g. ether groups and halogens such as chloride and bromine. Specific examples include methanol, ethanol, propanol, butanol, isobutyl alcohol, pentanol, hexanol, 2-ethylhexanol, cyclohexanol, cetylalcohol, cyclohexanol, benzylalcohol, 2-methoxyethanol, and 2-bromoethanol. Preferred alcohols are propanol, isobutyl alcohol, and pentanol.

In general, suitable aromatic alcohols for component (C) of the present invention include those compounds which contain from 6 to 10 carbon atoms and have one hydroxyl group directly attached to the aromatic ring. Examples of suitable aromatic alcohols include phenol, the cresols, the xylenols and the trimethylphenols.

When using component (C) in accordance with the invention, it is possible to premix components (B) and (C) prior to reacting with component (A) the diphenylmethane diisocyanate. However, it is possible to simply react component (A) the diphenylmethane diisocyanate, with components (B) and (C) without premixing components (B) and (C). When component (C) is present, the relative quantities of these two components should be such that the weight ratio of component (B) to component (C) ranges from 95.5% (B):4.5% (C) to 4.5% (B):95.5% (C). It is preferred that the weight ratio of component (B) to component (C) is from 70% (B):30% (C) to 30% (B):70% (C).

In accordance with the present invention, a suitable catalyst may be present. Some examples of such catalysts include, but are not limited to, zinc acetylacetonate, zinc 2-ethylhexanoate, and other common zinc compounds, tin octanoate, dibutyltin dilaurate, and other common tin compounds, cobalt naphthanate, lead linoresinate, titanium 2-ethylhexanoate and other titanium (IV) compounds, zirconium 2-ethylhexanoate and other common zirconium (IV) compounds, bismuth 2-ethylhexanoate and other common bismuth compounds. The catalyst is typically used in an amount of at least about 50 ppm, and preferably at least about 100 ppm, based on the weight of isocyanate compound. The catalyst is also typically used in an amount of less than or equal to 5000 ppm, and preferably of less than or equal to about 1000 ppm, based on the weight of the isocyanate compound. The catalyst may be present in an amount ranging between any combination of these upper and lower values, inclusive. For example, the catalyst may be present in an amount of from 50 ppm to 5000 ppm, and preferably from about 100 ppm to 1000 ppm, based on the isocyanate compound.

Generally, the process of preparing the liquid, storage stable di- and/or poly-isocyanates of the invention comprises reacting (A) a suitable diphenylmethane diisocyanate component, with (B) a compound selected from the group of amides, bisamides and cyclic ureas as described above in the presence of a catalyst. The reaction typically is at a temperature of at least about 50° C., and more preferably at least about 70° C. The reaction also typically is at a temperature of less than or equal to 150° C., and more preferably less than or equal to 120° C. The reaction may occur at a temperature between any combination of these upper and lower values, inclusive. For example, the reaction may occur at a temperature of from 50 to 150° C., and more preferably of from 70 to 120° C.

The modified isocyanate compositions of the present invention may be reacted with one or more isocyanate-reactive components to form, for example, polyurethanes and/or polyureas.

The following examples further illustrate details for the preparation of the compositions of this invention. The invention, which is set forth in the foregoing disclosure, is not to be limited either in spirit or scope by these examples. Those skilled in the art will readily understand that known variations of the conditions and processes of the following preparative procedures can be used to prepare these compositions. Unless otherwise noted, all temperatures are degrees Celsius and all parts and percentages are parts by weight and percentages by weight, respectively.

EXAMPLES

The following components were used in the working examples:

| | |
|---|---|
| ISO A: | 4,4'-diphenylmethane diisocyanate |
| Amide A: | N-methylacetamide |
| Amide B: | N-methylformamide |
| Urea A: | 2-imidazolidone |
| Catalyst A: | zinc acetylacetonate |
| Catalyst B: | tin octanoate |
| Catalyst C: | zinc 2-ethylhexanoate |

In a suitable flask, were added 250 g of Isocyanate A and the amide or urea compound, followed by heating to 60° C. under nitrogen. The catalyst (300 ppm) was added, and the mixture heated at 90° C. for 3.5 to 6 hours to reach theoretical % NCO. Table 1 shows the results.

TABLE 1

| Example | Amide/Urea | Catalyst | Time (h) | % NCO |
|---|---|---|---|---|
| 1 | Amide A (17 g) | Catalyst A | 4.8 | 24.6% |
| 2 | Amide A (17 g) | Catalyst B | 7 | 24.4% |
| 3 | Amide A (17 g) | Catalyst C | 6.5 | 23.4% |
| 4 | Amide B (11 g) | Catalyst A | 4.5 | 27.4% |
| 5 | Urea A (13 g) | Catalyst B | 3.5 | 23.8% |

All examples resulted in liquid MDI products at room temperature.

Table 2 shows a freezing point study for the liquid product of N-methylformamide and MDI at various % NCO. The freezing point of 4,4'-MDI is 42-44° C.

TABLE 2

| Example | % NCO | Freezing Point (° C.) |
|---|---|---|
| 6a | 27.2% | 7 |
| 6b | 26.6% | 5 |
| 6c | 24.6% | <1* |

*could not go below 1° C. with cooling bath

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A liquid, storage-stable diisocyanate having an NCO group content of 11 to 32% by weight, and comprising the reaction product of:
   (A) a diphenylmethane diisocyanate which comprises:
      (1) from 0 to 6% by weight of the 2,2'-isomer,
      (2) from 0 to 60% by weight of the 2,4'-isomer, and
      (3) from 34 to 100% by weight of 4,4'-isomer,
         wherein the sum of the %'s by weight of (1), (2) and (3) totals 100% by weight of (A) the diphenylmethane diisocyanate;
   with
   (B) at least one compound selected from the group consisting of:

(1) amides which correspond to the structure:

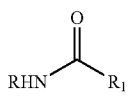
(I)

wherein:
R: represents a hydrogen atom, an alkyl radical containing from 1 to 6 carbon atoms, a cycloalkyl radical containing from 5 to 6 carbon atoms, or an aryl radical containing 6 carbon atoms;
and
$R_1$: represents a hydrogen atom, an alkyl radical containing from 1 to 6 carbon atoms, a cycloalkyl radical containing from 5 to 6 carbon atoms, an aryl radical containing 6 carbon atoms, or an alkoxy radical;
with the proviso that R and $R_1$ do not simultaneously represent hydrogen;
(2) bisamides which correspond to the structure:

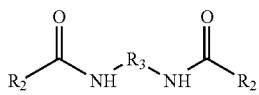
(II)

wherein:
each $R_2$: independently represents a hydrogen atom, an alkyl radical containing from 1 to 6 carbon atoms, a cycloalkyl radical containing 5 or 6 carbon atoms, an alkoxy radical, or an aryl radical containing 6 carbon atoms;
and
$R_3$: represents an alkyl radical containing from 1 to 12 carbon atoms or a cycloalkyl radical containing 6 carbon atoms;
and
(3) cyclic ureas which correspond to the structure:

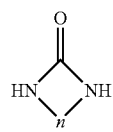
(III)

wherein:
n: represents from 2 to 5 methylene groups; in the presence of one or more catalyst.

2. The liquid, storage-stable diisocyanate of claim 1, wherein the reaction of (A) with (B) is in the presence of at least one catalyst, with the quantity of catalyst ranging from 50 to 5000 ppm, based on the weight of isocyanate.

3. The liquid, storage-stable diisocyanate of claim 1, in which the reaction of (A) with (B) is at a temperature of from 50 to 150° C.

4. The liquid, storage-stable diisocyanate of claim 1 having an NCO group content of about 14 to about 30% by weight, comprising the reaction product of (A), with a mixture comprising (B)(1) and (C) at least one component selected from the group consisting of aliphatic alcohols having from 1 to 32 carbon atoms and aromatic alcohols having from 1 to 10 carbon atoms, wherein the weight ratio of component (B) to component (C) ranging from 95.5%:4.5% to 4.5%:95.5%.

5. The liquid, storage-stable diisocyanate of claim 1, in which component (B) comprises (1) an amide which corresponds to structure (I), wherein R represents an alkyl radical containing from 1 to 3 carbon atoms; and $R_1$ represent an alkyl radical containing from 1 to 3 carbon atoms.

6. The liquid, storage-stable diisocyanate of claim 1, in which component (B) comprises (2) a bisamide which corresponds to structure (II), wherein $R_2$ represents an alkyl radical containing from 1 to 3 carbon atoms, and $R_3$ represents an alkyl radical containing from 2 to 6 carbon atoms.

7. The liquid, storage-stable diisocyanate of claim 1, wherein (B)(1) comprises N-methylformamide, N-ethylformamide, N-cyclo-hexylformamide, N-phenylformamide, acetamide, N-methylacetamide, N-ethylacetamide, N-methylpropionamide, N-methylcyclohexanecarboxamide, or N-methylbenzamide.

8. The liquid, storage-stable diisocyanate of claim 1, in which component (B)(2) comprises N,N'-ethylenebisformamide, N,N'-diacetyl-ethylenediamine, N,N'-ethylenebis(cyclohexanecarboxamide) N,N'-ethylenebisbenzamide, N,N'-bis(methoxycarbonyl)-1,2-ethanediamine, or N,N'-1,2-diacetylhexamethylenediamine.

9. The liquid, storage-stable diisocyanate of claim 1, in which component (B)(3) comprises imidazolidone, propyleneurea, or tetramethyleneurea.

10. The liquid, storage-stable diisocyanate of claim 1, in which
(A) said diphenylmethane diisocyanate comprises:
(1) from 0 to 2% by weight of the 2,2'-isomer,
(2) from 1 to 30% by weight of the 2,4'-isomer, and
(3) from 68 to 99% by weight of 4,4'-isomer,
wherein the sum of the %'s by weight of (1), (2) and (3) totals 100% by weight of (A) the diphenylmethane diisocyanate.

11. The liquid, storage-stable diisocyanate of claim 1, wherein components (A) and (B) are present in amounts such that there are from 0.01 to 0.5 equivalent of component (B) per equivalent of component (A).

12. A process for the preparation of a liquid, storage-stable diisocyanate comprising:
(1) reacting
(A) a diphenylmethane diisocyanate which comprises:
(1) from 0 to 6% by weight of the 2,2'-isomer,
(2) from 0 to 60% by weight of the 2,4'-isomer, and
(3) from 34 to 100% by weight of 4,4'-isomer,
wherein the sum of the %'s by weight of (1), (2) and (3) totals 100% by weight of (A) the diphenylmethane diisocyanate;
with
(B) at least one compound selected from the group consisting of:
(1) amides which correspond to the structure:

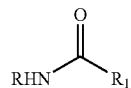
(I)

wherein:

R: represents a hydrogen atom, an alkyl radical containing from 1 to 6 carbon atoms, a cycloalkyl radical containing from 5 to 6 carbon atoms, or an aryl radical containing 6 carbon atoms; and $R_1$: represents a hydrogen atom, an alkyl radical containing from 1 to 6 carbon atoms, a cycloalkyl radical containing from 5 to 6 carbon atoms, an aryl radical containing 6 carbon atoms, or an alkoxy radical;

with the proviso that R and $R_1$ do not simultaneously represent hydrogen;

(2) bisamides which correspond to the structure:

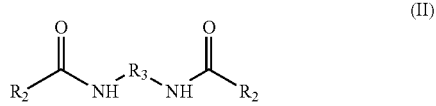

(II)

wherein:

each $R_2$: independently represents a hydrogen atom, an alkyl radical containing from 1 to 6 carbon atoms, a cycloalkyl radical containing 5 or 6 carbon atoms, an alkoxy radical, or an aryl radical containing 6 carbon atoms; and $R_3$: represents an alkyl radical containing from 1 to 12 carbon atoms or a cycloalkyl radical containing 6 carbon atoms;

and (3) cyclic ureas which correspond to the structure:

(III)

wherein:

n: represents from 2 to 5 methylene groups; in the presence of one or more catalyst.

13. The process of claim 12, wherein the reaction of (A) with (B) is in the presence of at least one catalyst, with the quantity of catalyst ranging from 50 to 5000 ppm, based on the weight of isocyanate.

14. The process of claim 12, in which the reaction of (A) with (B) is at a temperature of from 50 to 150° C.

15. The process of claim 12, having an NCO group content of about 14 to about 30% by weight, comprising the reaction product of (A), with a mixture comprising (B)(1) and (C) at least one component selected from the group consisting of aliphatic alcohols having from 1 to 32 carbon atoms and aromatic alcohols having from 1 to 10 carbon atoms, wherein the weight ratio of component (B) to component (C) ranging from 95.5%:4.5% to 4.5%:95.5%.

16. The process of claim 12, in which component (B) comprises (1) an amide which corresponds to structure (I) wherein R represents an alkyl radical containing from 1 to 3 carbon atoms, and $R_1$ represent an alkyl radical containing from 1 to 3 carbon atoms.

17. The process of claim 12, in which component (B) comprises (2) a bisamide which corresponds to structure (II) wherein $R_2$ represents an alkyl radical containing from 1 to 3 carbon atoms, and $R_3$ represents an alkyl radical containing from 2 to 6 carbon atoms.

18. The process of claim 12, wherein (B)(1) comprises N-methylformamide, N-ethylformamide, N-cyclohexylformamide, N-phenylformamide, acetamide, N-methylacetamide, N-ethylacetamide, N-methylpropionamide, N-methylcyclohexanecarboxamide, or N-methylbenzamide.

19. The process of claim 12, in which component (B)(2) comprises N,N'-ethylenebisformamide, N,N'-diacetylethylenediamine, N,N'-ethylenebis(cyclohexanecarboxamide), N,N'-ethylenebisbenzamide, N,N'-bis(methoxycarbonyl)-1, 2-ethanediamine, or N,N'-1,2-diacetylhexa-methylenediamine.

20. The process of claim 12, in which component (B)(3) comprises imidazolidone, propyleneurea, or tetramethyleneurea.

21. The process of claim 12, in which (A) said diphenylmethane diisocyanate comprises:
(1) from 0 to 2% by weight of the 2,2'-isomer,
(2) from 1 to 30% by weight of the 2,4'-isomer, and
(3) from 68 to 99% by weight of 4,4'-isomer,
wherein the sum of the %'s by weight of (1), (2) and (3) totals 100% by weight of (A) the diphenylmethane diisocyanate.

22. The process of claim 12, wherein components (A) and (B) are present in amounts such that there are from 0.01 to 0.5 equivalent of component (B) per equivalent of component (A).

* * * * *